US006358431B1

(12) United States Patent
Stirling et al.

(10) Patent No.: US 6,358,431 B1
(45) Date of Patent: *Mar. 19, 2002

(54) CALIXARENES

(75) Inventors: Charles James Matthew Stirling, Sheffield; Frank Davis, Caldervale, both of (GB)

(73) Assignee: The University of Sheffield, Sheffield (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/171,201

(22) PCT Filed: Apr. 15, 1997

(86) PCT No.: PCT/GB97/01036

§ 371 Date: Feb. 24, 1999

§ 102(e) Date: Feb. 24, 1999

(87) PCT Pub. No.: WO97/39077

PCT Pub. Date: Oct. 23, 1997

(30) Foreign Application Priority Data

Apr. 16, 1996 (GB) .............................. 9607886

(51) Int. Cl.[7] .............................. C14C 9/00; C07C 69/76
(52) U.S. Cl. ...................... 252/8.57; 252/8.62; 106/3; 560/36; 560/45; 560/46; 560/47; 560/48; 560/57; 560/75; 560/81; 560/83; 568/707; 568/709; 568/718; 568/720; 568/765

(58) Field of Search .............................. 560/36, 45, 46, 560/47, 48, 57, 75, 81, 83; 568/707, 709, 718, 720, 765; 252/8.57, 8.62; 106/3

(56) References Cited

U.S. PATENT DOCUMENTS 3,997,500 A * 12/1976 Vaughn ..................... 260/33.8
5,688,998 A * 11/1997 Ichimura et al. ............ 562/466

FOREIGN PATENT DOCUMENTS

EP    0 671 220 A    9/1995
JP    03 034955 A    4/1991

OTHER PUBLICATIONS

Van Velzen et al., "Self–Assembled Monolayers of Resorcin [4]arene Tetrasulfides on gold", Journal of the American Chemical Society, 117:6853–6862, 1995.

Patent Abstracts of Japan, vol. 15, No. 163, (C–0826), Apr. 24, 1991.

* cited by examiner

*Primary Examiner*—Rosalynd Keys
(74) *Attorney, Agent, or Firm*—Fish & Richardson P.C.

(57) ABSTRACT

A method of imparting a water repellent surface to a hydrophilic substrate which comprises contacting the substrate with a solution or dispersion of a suitable calixarene in a liquid medium.

10 Claims, No Drawings

CALIXARENES

This is a 371 of International Patent Application No. PCT/GB97/01036, with an international filing date of Apr. 15, 1997, now pending.

This invention relates to calixarenes, and more particularly to certain novel calixarenes, to a method of rendering substrate surfaces water repellent using calixarenes, and to substrates having water repellent surfaces produced thereby.

Calixarenes are amphiphilic molecules whose general structures is that of a molecular bowl on legs with the rim of the bowl lined by hydroxyl groups and the legs consisting of long chain alkyl groups. A detailed review of the different types of calixarenes and their methods of manufacture is given in Bohmer, Angew. Chem. Int. Ed. Engl. 1995, 34, 713–745, the entire disclosure of which is incorporated herein by reference for all purposes.

It has now been found that the hydroxyl groups lining the rim of the bowl of calixarenes can bond strongly to hydrophilic substrates and that if the calixarene also has hydrophobic pendant legs this can impart a highly water repellent surface to the substrate.

According to a first aspect of the invention, therefore, there is provided a method of imparting a water repellant surface to a hydrophilic substrate which comprises contacting the substrate with a solution or dispersion of a suitable calixarene in a liquid medium.

There are three main types of calixarene, prepared respectively from phenols, from resorcinols and from pyrogallols and aldehydes. Whilst the method of the invention is generally applicable to calixarenes, it is especially concerned with calixarenes derived from resorcinol, which in this specification will henceforth be termed "resorcarenes".

In another aspect, the present invention provides a new class of resorcarenes having the general structure I below:

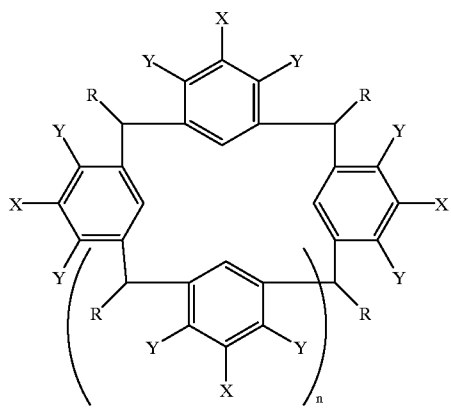

I wherein X is hydrogen, a $C_1$ to $C_4$ alkyl group, a substituted or unsubstituted amino group, or aminoalkyl group;

Y is OH or $OCH_2COOR'$, where R' is a $C_1$ to $C_4$ alkyl group;

R is a $C_1$ to $C_{18}$ fluoro-substituted alkyl group, and n is 1 or 3, and wherein each X, Y, R' and R group can be the same or different.

The method of the invention can be applied to a wide range of hydrophilic substrates including, for example, paper, cotton, wood, leather, stone, glass, hydrophilic synthetic fabrics, and hydrophilic polymeric materials.

Any suitable calixarene can be used in the method of the invention, provided that it has pendant legs imparting the desired water repellent properties to the substrate.

The pendant legs are preferably long chain hydrocarbon or fluorocarbon groups, having preferably from 5 to 15 carbon atoms in the chain, or long chain polyether groups. Long chain fluorocarbon groups are particularly preferred since these can impart both waterproofing and oil-proofing properties to a surface. The pendant legs preferably comprise long chain alkyl or fluoroalkyl groups, which terms, in this specification, include saturated and unsaturated (alkene and alkyne) groups, and which may also comprise other substituents.

Resorcarenes are particularly preferred for use in the method of the present invention, since it has been found that the water repellent properties imparted by these compounds are particularly persistent, and are not easily destroyed, for example, by washing. The resorcarenes are also particularly effective in imparting water repellency to rough surfaces. The most preferred resorcarenes for use in the method of the present invention are the new fluoro-substituted resorcarenes described hitherto.

Without intending the invention to be bound by any particular theory, it is believed that the improved water repellent properties obtained using calixarenes may be due to their ability to form multilayers in thin fibres. This property is described in relation to resorcarenes by Davis & Sterling in J. Am. Chem. Soc. 1995, 117, 10385–10386.

Certain preferred resorcarenes for use in the present invention have pendent legs comprising unsaturated hydrocarbon chains. Some of these compounds are new and accordingly comprise a further aspect of the invention. The presence of double bonds in the unsaturated chains provides the possibility for cross-linking reactions to be initiated, which could, for example, improve the binding of the resorcarene to the substrate surface, or improve the strength of the film (multilayer) if present, or provide sites for binding other reactive groups onto the resorcarene. Cross linking can be accomplished, for example, by the use of ultraviolet light, or by other free radical generating cross linking methods.

Preferably the resorcarene is one in which X is hydrogen. Other preferred resorcarenes for use in the present invention are those in which:

|  | Compound |
|---|---|
| R = —$(CH_2)_8CH{=}CH_2$; X = H | II |
| R = —$C_{11}H_{23}$; X = H | III |
| R = —$C_5H_{11}$; X = H | IV |
| R = —$CH_2C_8F_{17}$; X = H | V |
| R = —$C_{11}H_{23}$; X = —$CH_2N(CH_2C_6H_5)_2$ | VI |
| R = —$(CH_2)_8C{\equiv}CH$; X = H | VII |

In the method of the invention, the calixarene solution or dispersion can simply be sprayed onto the substrate, or the substrate can be dipped into the solution or dispersion as appropriate. The calixarene is preferably applied dissolved or dispersed in a hydrophobic organic solvent, for example, hexane, dichloromethane or toluene.

The new resorcarenes having fluorinated pendant legs are preferably applied in solution or dispersion in an acetone/ethanol mixture.

The method can be carried out at any suitable temperature, although ambient temperatures are usually sufficient and heating is not normally necessary.

The concentration of the calixarene in solution can be, for example, from 0.001 to 10% by weight, but is preferably from 0.01 to 5% and more preferably around 0.1 to 1% by weight, based on the weight of the solution.

The invention is illustrated by the following Examples:

EXAMPLE 1

This Example describes the preparation of compound II.

Resorcinol (5.5 g) and 10-undecenal (8.4 g) are dissolved in ethanol (40 ml). Concentrated HCl (3 ml) is added and the solution refluxed under argon for 17 hours to give a reddish solution and a deep orange solid. The reddish solution is poured into 500 ml of water and a orange product filtered off. This product is recrystallized twice from 50:50 acetone/ 40–60 petroleum ether and dried under vacuum to give the monohydrate, (6.3 g, 49%) mp>250° C. (Lit, 270° C.). NMR is consistent with that of a tetramer, peaks at 9.6,9.3 (phenols), 7.2,6.1 (aromatics), 4.5, 4.95 (alkenes and water), 4.25 (Ar—C—H), 2.25, 2.05, 1.6 (methylenes). Elemental analysis C 76.82% H 9.50% (Calc. for monohydrate C 77.12%, H 9.26%). Fast atom bombardment mass spectroscopy (FAB) shows molecular ion at 1040 as expected for a tetramer.

EXAMPLE 2

This Example describes the preparation of Compound III.

Resorcinol (5.5 g) and dodecanal (9.2 g) are dissolved in ethanol (40 ml). Concentrated HCl (3 ml) is added and the solution refluxed under argon for 17 hours to give a reddish solution. The reddish solution is poured into 500 ml of water and an orange product filtered off. This product is recrystallized twice from 50:50 acetone/40–60 petroleum ether and dried under vacuum. The results indicate the resorcarene forms the monohydrate, (10.5 g, 74%), m.p.>250° C. (Lit. 270° C.). NMR is consistent with that of the tetramer. Peaks at 9.6, 9.3 (phenols), 7.2,6.1 (aromatics), 4.95 (water), 4.25 (Ar—C—H), 2.25, 2.05, 1.6 (methylenes), 0.9 (methyl). Elemental analysis C 78.04% H 10.32% (Calc. for monhydrate C 78.21%, H 10.21%). FAB shows molecular ion at 1104 as expected for a tetramer.

EXAMPLE 3

This Example describes the preparation of Compound IV.

Resorcinol (5.5 g) and hexanol (5.0 g) are dissolved in ethanol (40 ml). Concentrated HCl (3 ml) is added and the solution refluxed under argon for 17 hours to give a reddish solution. The reddish solution is poured into 500 ml of water and an orange product filtered off. This product is recrystallized twice from ethanol and dried under vacuum. The results indicate the resorcarene forms the monohydrate (8.0 g, 82%), mp>250° C. (Lit, >315° C.). NMR is consistent with that of the tetramer. Peaks at 9.6,9.3 (phenols), 7.2,6.1 (aromatics), 4.95 (water), 4.25 (Ar—C—H), 2.25, 2.05, 1.6 (methylenes), 0.9 (methyl). FAB shows molecular ion at 768 as expected for a tetramer. Elemental analysis C 74.81% H 8.51% (Calc. for monohydrate C 74.97%, H 8.39%).

EXAMPLE 4

This Example describes the preparation of Compound V.

1H, 2H, 2H, perfluorodecanal diethyl acetal (1.07 g) (FluoroChem), resorcinol (0.22 g), chloroform (10 ml) and trifluoroacetic acid (1 ml) are combined and stirred at room temperature overnight. A yellow solid product precipitates (1.0 g, 98%) and can be recrystallized from trifluorethanol. The FTIR, NMR and FAB spectra are all consistent with formation of the cyclic tetramer.

EXAMPLE 5

This Example describes the preparation of Compound VI.

The resorcarene prepared according to Example 2 (1.10 g), paraformaldehyde (0.18 g), ethanol (60 ml) and dibenzylamine (1.17 g) are refluxed together under Ar for 16 hours. The compound precipitates as formed and is recrystallised with toluene to give a white solid, (1.9 g, 96%) mpt >250° C. NMR clearly shows loss of the 2-proton and appearance of the benzyl group. FAB 1943 (1944), elemental analysis: C 81.3%, H 8.9%, N 3.0% (Calc. C 81.6%, H 8.9%, N 2.9%).

EXAMPLE 6

This Example demonstrates the use of calixarenes according to the invention in imparting water repellency to a variety of substrate surfaces.

The remarkable waterproofing properties of the calixarenes can be established using experiments carried out under simple conditions. As an example, the calixarene produced from dodecanal and resorcinol is made up as a 1% solution in hexane and samples to be treated are either quickly dipped in the solution, as in the case of paper, leather, and cotton wool, or by application in the case of stone, glass and wood, and allowing the solution to evaporate or soak into the surface.

The waterproofing property is then assessed by comparison with untreated specimens or untreated areas of the same specimen in each case by an application of small drops (circa 0.1 ml) of ordinary tap water. The change of contact angle assessed with the naked eye is then observed as a function of time where flat surfaces of the specimens are appropriately available. This applies to paper, leather, wood, stone and glass specimens particularly and, for example, the contact angle of a drop of water on treated wood remains at approximately 110° for about 1 hour, whereas, in the untreated portion of the same specimen, the contact angle decreases from the time of deposition and soaking in of the drop is typically complete in around 5 minutes. In the case of waterproofed paper, highly absorbent kitchen paper was used to make an exacting test, the untreated paper when placed on the surface of water sinks at once, whereas treated paper has remained afloat for at least three weeks.

In the case of the calixarene with perfluorinated legs of Example 4, the compound has been made up as a saturated (circa 0.1% solution) in acetone and applied to both paper and to cotton wool. In both cases there is very marked water repellency and while, for example, untreated cotton wool sinks at once in water, it is impossible to immerse the waterproofed specimen of cotton wool.

A further demonstration of the water repellent effect of the compounds of the invention is in the waterproofing of sugar. Icing sugar treated with the calixarene of Example 1 floats briefly on the surface of water while untreated icing sugar sinks at once and cubed sugar allowed to soak up 1% solution of the calixarene and then dried takes some 20 minutes before breaking down under the surface of water. The untreated cube collapses in roughly 30 seconds.

A particular advantage of the method of the present invention is that the properties of the substrate can, in preferred embodiments, remain otherwise unaffected by the water repellency treatment. Thus, without wishing to be bound by any particular theory, it is believed that the calixarenes can become attached to the substrate by hydrogen bonding without the need to break covalent bonds at the substrate surface, as is the case with many chemical waterproofing treatments.

A further advantage of the calixarene treatment is that the molecule are too big to penetrate a cell membrane and thus have a low risk of toxicity if ingested.

A still further advantage of the calixarene treatment is that the pendant hydrocarbon groups may impart lubricating properties to the surface. However, an attempt to waterproof iron using solvent washed steel wool as a test material gave no evidence of water repellency. The treated and untreated specimens of steel wool rusted under water in air at approximately comparable rates.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiments. The invention extends to any novel one, or any novel combination, of the features disclosed in this specification (including any accompanying claims, abstract and drawings), or to any novel one, or any novel combination, of the steps of any method or process so disclosed.

What is claimed is:

1. A method of imparting a water repellant surface to a hydrophilic substrate which comprises contacting the substrate with a solution or dispersion of a suitable resorcarene in a liquid medium, said resorcarene having the general structure I below:

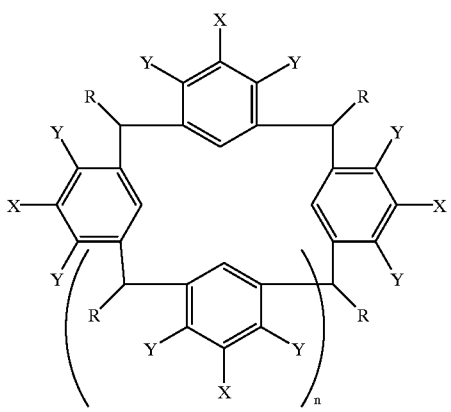

where
X is hydrogen, a $C_1$ to $C_4$ alkyl group, a substituted or unsubstituted amino group, or alkylamino group;

Y is OH or $OCH_2COOR'$, where R' is a $C_1$ to $C_4$ alkyl group;

R is a $C_1$ to $C_{18}$ fluoro-substituted alkyl group; and n is 1 or 3;

wherein each X, Y, R' and R group can be the same or different.

2. A method according to claim 1, in which the substrate comprises paper, cotton, wood, leather, stone, glass, a hydrophilic synthetic fabric, or a hydrophilic polymeric material.

3. A method according to claim 1, in which the resorcarene has pendant legs comprising unsaturated hydrocarbon chains, and cross-linking of the unsaturated groups in the hydrocarbon chains is carried out.

4. A method according to claim 1, in which the resorcarene is applied to the substrate in solution or dispersion in a suitable solvent.

5. A method according to claim 4, in which the solvent comprises a hydrophobic organic solvent.

6. A method according to claim 4, in which the concentration of the resorcarene in the solution is from 0.01 to 5% by weight, based on the weight of the solution.

7. A method according to claim 5, in which the concentration of the resorcarene in the solution is from 0.01 to 5% by weight, based on the weight of the solution.

8. A resorcarene having the general structure I below:

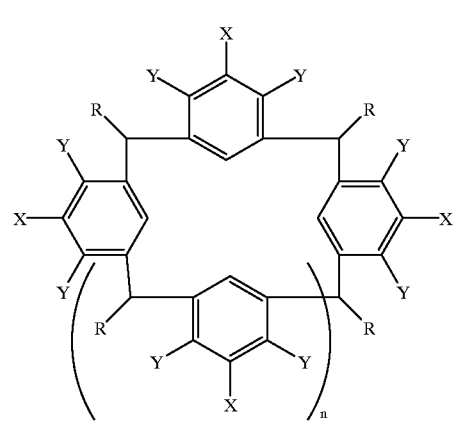

wherein X is hydrogen, a $C_1$ to $C_4$ alkyl group, or a substituted or unsubstituted amine group;

Y is OH or $OCH_2COOR'$, where R' is a $C_1$ to $C_4$ alkyl group;

R is a $C_1$ to $C_{18}$ fluoro-substituted alkyl group, and n is 1 or 3, and wherein each X, Y, R' and R group can be the same or different.

9. A resorcarene according to claim 8, in which X is hydrogen.

10. A resorcarene according to claim 8, wherein R=—$CH_2C_8F_{17}$ and X=H.

* * * * *